United States Patent [19]

Klauke et al.

[11] Patent Number: 4,555,370
[45] Date of Patent: Nov. 26, 1985

[54] PROCESS FOR THE PREPARATION OF ACYL CYANIDES

[75] Inventors: Erich Klauke; Kurt Findeisen, both of Odenthal, Fed. Rep. of Germany

[73] Assignee: Bayer Aktiengesellschaft, Leverkusen, Fed. Rep. of Germany

[21] Appl. No.: 658,444

[22] Filed: Oct. 5, 1984

Related U.S. Application Data

[63] Continuation of Ser. No. 487,242, Apr. 27, 1983, abandoned, which is a continuation of Ser. No. 252,717, Apr. 10, 1981, abandoned.

[30] Foreign Application Priority Data

Apr. 23, 1980 [DE] Fed. Rep. of Germany ....... 3015587

[51] Int. Cl.$^4$ .......................................... C07C 121/76
[52] U.S. Cl. ................................................. 260/545 R
[58] Field of Search ..................................... 260/545 R

[56] References Cited

U.S. PATENT DOCUMENTS

| | | | |
|---|---|---|---|
| 4,108,875 | 8/1978 | Klenk et al. | 260/545 R |
| 4,108,877 | 8/1978 | Klenk et al. | 260/545 R |
| 4,117,008 | 9/1978 | Klenk et al. | 260/545 R |
| 4,143,068 | 3/1979 | Findeisen | 260/545 R |
| 4,209,462 | 6/1980 | Photis | 260/545 R |
| 4,238,413 | 12/1980 | Tang et al. | 260/545 R |
| 4,339,591 | 7/1982 | Kleeman et al. | 260/545 R X |

FOREIGN PATENT DOCUMENTS

| | | |
|---|---|---|
| 2614240 | 10/1977 | Fed. Rep. of Germany . |
| 2614242 | 10/1977 | Fed. Rep. of Germany . |
| 2642140 | 3/1978 | Fed. Rep. of Germany . |
| 2708183 | 8/1978 | Fed. Rep. of Germany . |
| 0029526 | 8/1979 | Japan .............................. 260/545 R |

OTHER PUBLICATIONS

Koenig et al., Tetrahedron Letters, No. 26, pp. 2275–2278 (1974).

Primary Examiner—Ethel G. Love
Attorney, Agent, or Firm—Felfe & Lynch

[57] ABSTRACT

A novel process for the preparation of acyl cyanides of the general formula $$R-CO-CN \qquad (I)$$

wherein
R represents an optionally substituted alkyl radical with 1 to 8 carbon atoms, an optionally substituted cycloalkyl radical with 3 to 12 carbon atoms, an optionally substituted aryl radical or an optionally substituted 5-membered or 6-membered heterocyclic radical, which can additionally be fused to a benzene ring, in which a carboxylic acid fluoride or the general formula $$R-CO-F \qquad (II)$$

in which
R has the abovementioned meaning
is reacted with an alkali metal cyanide, optionally in the presence of a diluent, at a temperature between 10° and 200° C.

The acylcyanides (I) can be used as intermediates in the synthesis of known herbicides.

19 Claims, No Drawings

PROCESS FOR THE PREPARATION OF ACYL CYANIDES

This application is a continuation of application Ser. No. 487,242, filed Apr. 27, 1983, which is a continuation of application Ser. No. 252,717, filed Apr. 10, 1981, both abandoned.

This invention relates to a new process for the preparation of acyl cyanides. Such materials are useful in the synthesis of herbicides.

It is known that acyl cyanides can be obtained if carboxylic acid halides are reacted with alkali metal cyanides at temperatures between 100° and 300° C. in the presence of catalytic amounts of a heavy metal cyanide, for example, copper cyanide, and optionally in the presence of a diluent (see DE-OS (German Published Specification) No. 2,614,242). However, a disadvantage of this process is the need to employ heavy metal cyanides as the catalyst (regarding the older prior art, see J. Thesing et al., Angew. Chem. 68, pages 425–435 (1956)).

The present invention now provides a process for the preparation of acyl cyanides of the general formula

R—CO—CN    (I)

in which
R represents an optionally substituted alkyl radical with 1 to 8 carbon atoms, an optionally substituted cycloalkyl radical with 3 to 12 carbon atoms, an optionally substituted aryl radical or an optionally substituted 5-membered or 6-membered heterocyclic radical, which can additionally be fused to a benzene ring, in which a carboxylic acid fluoride of the general formula

R—CO—F    (II)

in which
R has the abovementioned meaning
is reacted with an alkali metal cyanide, optionally in the presence of a diluent, at a temperature between 10° and 200° C. The process of the present invention produces the acyl cyanides of formula (I) in high yields and in high purity.

It must be described as definitely surprising that acyl cyanides of the formula (I) are obtainable in high yield and excellent purity by the process according to the invention. It is particularly surprising that the carboxylic acid fluorides react with alkali metal cyanides under milder conditions than the corresponding carboxylic acid chlorides, namely without heavy metal cyanide as the catalyst and at relatively low temperatures.

It is known that the usual carboxylic acid fluorides are in every case less reactive than the other carboxylic acid halides, including carboxylic acid chlorides (see Houben-Weyl, Methoden der Organischen chemie (Methods of Organic Chemistry), 4th edition, volume V/3, page 419 (1962)). In view of the known prior art, it was therefore to be expected that carboxylic acid fluorides could only be reacted under more severe reaction conditions, along the same lines as the carboxylic acid chlorides, and that without addition of a heavy metal cyanide as the catalyst virtually no reaction of the carboxylic acid fluorides with the alkali metal cyanides would occur.

The process according to the invention has a number of advantages. An important advantage is that no copper salts or other heavy metal salts need be employed in the preparation. Furthermore, it is an advantage that the process according to the invention takes place under milder conditions than the process previously known from DE-OS (German Published Specification) No. 2,624,242; while in the case of the previously known process the optimum reaction temperatures are in every case in the region of 200° C. or above, they are of the order of 100° C. or lower in the process according to the invention, as is shown by the relevant Preparative Examples. Furthermore, the process according to the invention is not restricted to the synthesis of a small number of specific compounds but can be employed very broadly. Quite apart from this, it can be carried out in a relatively simple manner even on an industrial scale. As already mentioned, the acyl cyanides are obtained, in the process according to the invention, in high yield and excellent purity, free from interfering by-products.

If benzoyl fluoride and sodium cyanide are used as starting materials, the course of the reaction according to the present invention is illustrated by the following equation:

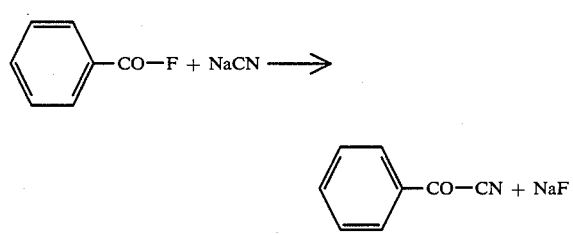

Preferred carboxylic acid fluorides used as starting materials of formula (I) are those in which R represents an alkyl radical with 4 to 6 carbon atoms optionally substituted by alkoxy with 1 to 4 carbon atoms, carbalkoxy with 1 to 4 carbon atoms in the alkoxy group, nitro, nitrile and/or halogen (for example fluorine, chlorine, bromine or iodine), represents a cycloalkyl radical with 3 to 6 carbon atoms in the ring system, which is optionally substituted by alkyl, alkoxy or carbalkoxy each with up to 4 carbon atoms, nitro, nitrile and/or halogen (for example, fluorine, chlorine or bromine), represents an aryl radical, especially a phenyl or naphthyl radical, which is optionally substituted by alkyl, alkoxy, haloalkyl, haloalkoxy or carbalkoxy, each with up to 4 carbon atoms, nitro and/or halogen (for example, fluorine, chlorine or bromine), or represents a substituted 5-membered or 6-membered heterocyclic radical, which contains 1 to 3 hetero-atoms, such as oxygen, sulphur and/or nitrogen, in the ring and is optionally furthermore fused to a benzene ring, and is optionally substituted by alkyl, alkoxy or carbalkoxy, each with up to 4 carbon atoms, nitro, nitrile and/or halogen (for example fluorine, chlorine and bromine).

As examples of heterocyclic radicals which are in particular suitable as radicals R there may be mentioned: morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

The carboxylic acid fluorides of the formula (II) to be used as starting materials are known or can be prepared in accordance with methods which are known in principle, for example by reacting the corresponding carboxylic acid chlorides with hydrogen fluoride or alkali metal fluorides or alkali metal hydrogen fluorides (see Houben-Weyl, Methoden der Organischen chemie (Methods of Organic Chemistry), 4th Edition, volume V/3, pages 119–120 and 148–150 (1962) as well as the Preparative Examples).

The following may be mentioned specifically as preferred examples of carboxylic acid fluorides of formula (II): pivaloyl fluoride, hexanecarboxylic acid fluoride, cyclopropanecarboxylic acid fluoride, (2,2-dichloro-1-methylcyclopropyl)-carboxylic acid fluoride, (2,2-dichloro-1,3-dimethylcyclopropyl)-carboxylic acid fluoride, cyclopentanecarboxylic acid fluoride, cyclohexanecarboxylic acid fluoride, benzoyl fluoride, 3-chlorobenzoyl fluoride, 4-chloro-benzoyl fluoride, 2,5-dichlorobenzoyl fluoride, 2-fluorobenzoyl fluoride, 2,6-difluorobenzoyl fluoride, 3-trifluoromethyl-benzoyl fluoride, 4-trifluoromethyl-benzoyl fluoride, 3-chloro-4-trifluoromethoxy-benzoyl fluoride, 3-bromo-4-fluorobenzoyl fluoride, 4-nitrobenzoyl fluoride, 3,5-dinitrobenzoyl fluoride, 3-nitro-4-methyl-benzoyl fluoride, 4-methyl-benzoyl fluoride, naphthalene-1-carboxylic acid fluoride, 1-phenyl-pyrazol-5-one-3-carboxylic acid fluoride and the additional carboxylic acid fluorides mentioned in the examples. Pivaloyl fluoride, benzoyl fluoride and 3-trifluoro-methyl-benzoyl fluoride are especially preferred.

Of course it is also possible to employ dicarboxylic acid difluorides, in appropriate amount, as carboxylic acid fluorides of formula (II) in which the radical —CO—F is a substituent on radical R, in the process according to the invention. As examples of these dicarboxylic acid difluorides, terephthalic acid difluoride and isophthalic acid difluoride may be mentioned.

As particularly preferred carboxylic acid fluorides of formula (II), benzoyl fluoride, 3-trifluoromethyl-benzoyl fluoride and pivaloyl fluoride may be mentioned.

Suitable alkali metal cyanides are especially sodium cyanide and potassium cyanide. Sodium cyanide is used preferentially.

The reaction according to the invention can be carried out in the presence or in the absence of a diluent.

Suitable diluents are any of the inert organic solvents which do not undergo a chemical reaction either with the carboxylic acid fluorides or with the alkali metal cyanides. As examples of such solvents there may be mentioned: methylene chloride, chloroform, ethyl acetate, glycol dimethyl ether, acetonitrile, sulpholane, toluene, xylene, chlorobenzene and dichlorobenzene.

Furthermore it is possible to use excess carboxylic acid fluoride of formula (II) as the diluent.

The reaction temperatures can be varied within the substantial range as stated above, of between 10° and 200° C., and when working in the presence of a diluent the temperature is preferably between 20° and 150° C., and when working without a diluent the temperature is preferably between 60° and 120° C., particularly preferentially between 80° and 100° C.

The process according to the invention is in general carried out under normal pressure. However, in the reaction of low-boiling carboxylic acid fluorides it is advisable to employ superatmospheric pressure, in general up to 15 bar, in order to increase the conversion.

In carrying out the process according to the invention, 0.7 to 1.4 moles of alkali metal cyanide, preferably 0.8 to 1.3 moles of alkali metal cyanide, are in general employed per mole of carboxylic acid fluoride of formula (II). A molar ratio of carboxylic acid fluoride of formula (II) to alkali metal cyanide of 1:1–1.25 is particularly preferred.

The working up of the reaction mixture is carried out, after completion of the reaction, in the usual manner. First, the alkali metal fluorides formed in the course of the reaction are separated off by filtration; they can be re-used to prepare the carboxylic acid fluorides of formula (II). The filtrate is subjected to a simple fractional distillation if liquid acyl cyanides of formula (I) are to be isolated.

Solid acyl cyanides of formula (I) are most appropriately obtained by crystallization from the reaction solution which has, where appropriate, been filtered hot and, where appropriate, been concentrated by distilling off of diluent; further purification by recrystallization can normally be dispensed with.

In a special variant of the process, the reaction according to the invention can also be carried out continuously.

The acyl cyanides of the formula (I) which can be prepared by the process according to the invention are valuable starting materials, for example for the synthesis of 1,2,4-triazin-5-ones, which possess outstanding herbicidal properties (see, for example, DE-OS (German Published Specification) No. 2,224,161; German Patent Specification No. 1,795,784).

Thus, for example, 3-methyl-4-amino-6-phenyl-1,2,4-triazine-5(4H)-one, of the formula

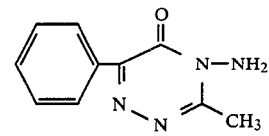

can be prepared if, in a first stage, benzoyl cyanide is reacted with ethanol in the presence of concentrated hydrochloric acid and the phenylglyoxylic acid ethyl ester thereby produced is reacted, in a second stage, with acetylhydrazine, whereupon 1-phenylglyoxylic acid ethyl ester 2-acetylhydrazone is formed, which, in a third stage, is converted, by means of hydrazine hydrate in the presence of pyridine, to the end product mentioned above.

This multi-stage synthesis can, in terms of formulae, be represented as follows:

1st Stage:

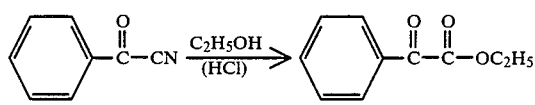

2nd Stage:

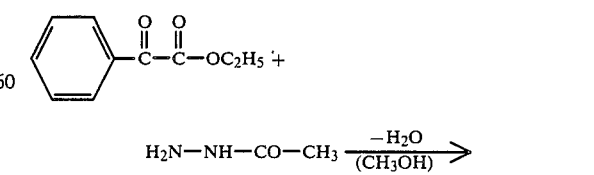

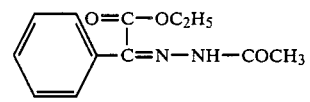

3rd Stage:

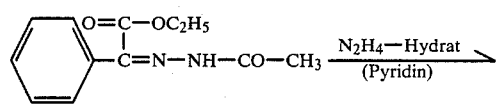

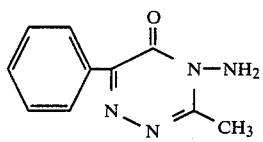

The pivaloyl cyanide which can be prepared according to the invention can be converted, in accordance with known processes, into, for example, the herbicidal active compound 3-methylthio-4-amino-6-tert.-butyl-1,2,4-triazin-5-(4H)-one (see DE-OS (German Published Specification) No. 2,733,180, U.S. Pat. No. 4,175,188 and also German Patent Application Nos. P 30 02 203.8, P 30 03 541.7 and P 30 09 043.8).

The process according to the invention is illustrated by the Preparative Examples which follow:

PREPARATIVE EXAMPLES

Example 1

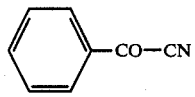

62 g of benzoyl fluoride (0.5 mole) and 25 g of sodium cyanide (0.5 mole) were added to 100 ml of acetonitrile in a 250 ml three-necked flask. The mixture was stirred and the internal temperature rose to 55° C. When the exothermic reaction had subsided, the mixture was boiled under reflux for three hours. It was then subjected to fractional distillation.

Yield: 63.5 g (97% of theory) of benzoyl cyanide; melting point: 33° C.

Example 2

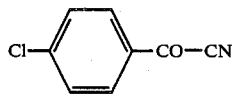

79.3 g of 4-chloro-benzoyl fluoride (0.5 mole) were introduced into 100 ml of toluene in a 250 ml three-necked flask equipped with a stirrer, thermometer and reflux condenser, and 25 g of sodium cyanide (0.5 mole) were then added. The internal temperature rose to 50° C. while the mixture was being stirred; thereafter, the mixture was warmed to 110° C. for 2 hours. The reaction mixture was freed from the sodium fluoride by filtration and was then distilled.

Yield: 81 g (98% of theory) of 4-chloro-benzoyl cyanide; boiling point: 117°-119° C. at 16 mbar.

Example 3

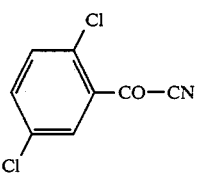

92.5 g of 2,5-dichloro-benzoyl fluoride (0.5 mole), 25 g of sodium cyanide (0.5 mole) and 100 ml of xylene were mixed, with stirring, in a 250 ml three-necked flask. When the exothermic reaction had subsided, the mixture was warmed under reflux for 1 hour. The sodium fluoride formed was filtered off, the filtrate was freed from the solvent and the residue was distilled.

Yield: 92 g (92% of theory) of 2,5-dichlorobenzoyl cyanide; boiling: 142°-145° C. at 19.5 mbar.

Example 4

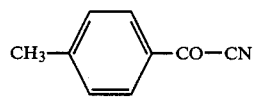

68.5 g of p-methyl-benzoyl fluoride (0.5 mole) and 25 g of sodium cyanide (0.5 mole) were introduced into 100 ml of methylene chloride in a 250 ml three-necked flask. After completion of the exothermic reaction, the mixture was warmed to the boil for 5 hours, and was then filtered and distilled.

Yield: 68 g (94% of theory) of p-methyl-benzoyl cyanide; boiling point: 114°-117° C. at 16 mbar; melting point: 46°-47° C.

Example 5

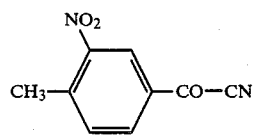

78.5 g of 3-nitro-4-methyl-benzoyl fluoride (0.5 mole), 25 g of sodium cyanide (0.5 mole) and 100 ml of chlorobenzene were mixed in a 250 ml three-necked flask. The mixture was then boiled for three hours under reflux. Thereafter, the solution was filtered and concentrated and the residue was recrystallized from isobutanol.

Yield: 83 g (87% of theory) of 3-nitro-4-methyl-benzoyl cyanide; melting point: 140°-142° C.

Example 6

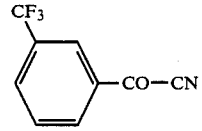

100 g (0.52 mole) of 3-trifluoromethyl-benzoyl fluoride were taken and 31 g (0.63 mole) of sodium cyanide were introduced. The reaction which commenced was slightly exothermic and the reaction mixture assumed a yellow discoloration. It was then heated to 90° C. in the course of 30 minutes and was stirred for a further 2 hours at this temperature. The change in refractive index in the course of the reaction was a good measure of the conversion; it changed from $n_D^{20}$: 1.4390 to 1.4745. For working up, the mixture was cooled and filtered and the filtrate was distilled.

93 g (90% of theory) of 3-trifluoromethyl-benzoyl cyanide were obtained as a water-clear liquid of boiling point 93° C./19 mbar and of refractive index $n_D^{20}$: 1.4779.

The acyl cyanides (I) listed in the table which follows could be prepared, starting from the corresponding carboxylic acid fluorides (II), under the same reaction conditions; the physical data are in each case indicated for the starting materials and the end products:

TABLE $$R-CO-F \longrightarrow R-CO-CN$$
$$(II) \qquad\qquad (I)$$

| Example No. | R | Boiling point/pressure Refractive index, $n_D^{20}$ Melting point (m.p.) where appropriate | |
|---|---|---|---|
| | | (II) | (I) |
| 7 | CF₃O—⟨⟩— | 94–95° C./100 mbar 1.4315 | 99° C./23 mbar 1.4775 |
| 8 | CF₃O—⟨⟩ | 53° C./14.6 mbar 1.4270 | 94° C./20 mbar 1.4688 |
| 9 | ⟨⟩—OCF₃ | 60° C./14.6 mbar 1.4285 | 104° C./19 mbar 1.4742 |
| 10 | ⟨⟩—CF₃ | 70° C./22 mbar 1.4429 | 109° C./20 mbar m.p. 58–59° C. |
| 11 | CF₃—⟨⟩— | 159° C./1 bar 1.4399 | 92° C./20 mbar 1.4772 |
| 12 | ⟨⟩—F | 171° C./1 bar 1.4865 | 111° C./22 mbar 1.5333 |
| 13 | F—⟨⟩ | 40° C./20 mbar 1.4764 | 88° C./20 mbar 1.5272 |
| 14 | F—⟨⟩— | 52° C./18.6 mbar 1.4792 | 93° C./20 mbar m.p. 23–24° C. |
| 15 | F—⟨⟩—F | 53° C./17.3 mbar 1.4680 | 101° C./21 mbar 1.5193 |
| 16 | CF₃—⟨⟩—Cl | 75° C./14.6 mbar 1.4659 | 115° C./20 mbar 1.5030 |

TABLE-continued $$R-CO-F \longrightarrow R-CO-CN$$
$$(II) \qquad\qquad (I)$$

| Example No. | R | Boiling point/pressure Refractive index, $n_D^{20}$ Melting point (m.p.) where appropriate | |
|---|---|---|---|
| | | (II) | (I) |
| 17 | CF₃O—⟨⟩—Cl | 78° C./18.6 mbar 1.4545 | 113° C./20 mbar 1.4941 |
| 18 | F—⟨⟩—Cl | 72° C./16 mbar 1.5070 | 114° C./18 mbar 1.5539 |
| 19 | F—⟨⟩—Br | 83° C./15 mbar m.p.: 32–40° C. | 126° C./20 mbar 1.5769 |
| 20 | F₅—⟨⟩ (pentafluoro) | 140° C./1 bar 1.4270 | 90° C./19 mbar 1.4700 |

Example 21

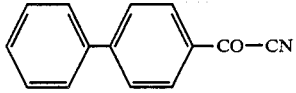

20 g of p-diphenylcarboxylic acid fluoride (0.1 mole) were dissolved in 60 ml of toluene in a 250 ml three-necked flask and 5.5 g of sodium cyanide (0.11 mole) were added. The reaction mixture was boiled for three hours under reflux and was filtered hot. After cooling, p-diphenylcarboxylic acid cyanide crystallized out from the toluene solution.

Yield: 19.7 g (96% of theory) of p-diphenylcarboxylic acid cyanide; melting point: 129° C.

Example 22

Following the procedure described above, 11 g of sodium cyanide (0.22 mole) were added to a solution of 20.8 g of pivaloyl fluoride (0.2 mole) in 50 ml of benzonitrile. An exothermic reaction occurred. Thereafter the internal temperature was raised to 130° C. and the mixture was stirred for 30 minutes at this temperature. When the mixture had cooled, the sodium fluoride was filtered off; the residue was distilled, first under normal pressure and then in vacuo.

Yield: 20.4 g (92% of theory) of pivaloyl cyanide; boiling point: 47°–52° C. at 20 mbar.

Examples of the preparation of carboxylic acid fluorides of formula (II):

Example a

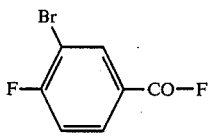

1,270 g (5 moles) of 4-chloro-3-bromo-benzoyl chloride, 1,150 g of tetramethylenesulphone and 315 g (7.5 moles) of anhydrous sodium fluoride were warmed for 5 hours to 210° C., while stirring. Thereafter, 435 g (7.5 moles) of anhydrous potassium fluoride, suspended in 1,150 g of tetramethylenesulphone, were added to the reaction mixture, and the latter was stirred for a further 7 hours at 210° C. The subsequent distillation gave 873 g (79% of theory) of 4-fluoro-3-bromobenzoyl fluoride (a starting material for Example 19).

Example b

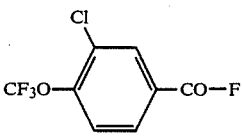

230 g of p-anisic acid and 230 g of thionyl chloride were gradually warmed to 60° C., under nitrogen. The reaction mixture was stirred for 10 hours at 60° C. Thereafter, excess thionyl chloride was stripped off in vacuo. The product which remained was chlorinated at 150° C. under UV irradiation. The reaction was complete after raising the temperature to 190° to 200° C. after a total of about 5 hours. 5 g of antimony pentachloride were added to the product which remained. Chlorine was passed into the mixture at 80°-100° C. until the calculated amount (1 mole equivalent) had been taken up. 453 g of crude product, $n_D^{20}$: 1.5825, were obtained. The crude product was added to 500 ml of anhydrous hydrofluoric acid in a steel autoclave and heated to 140° C., while stirring. The hydrogen chloride formed was released at about 21 bar. When the evolution of gas has ceased, the product was distilled in vacuo.

300 g of 3-chloro-4-trifluoromethoxy-benzoyl fluoride (a starting material for Example 17) were obtained.

Example c (CH$_3$)$_3$C—CO—F 100 ml of pivaloyl chloride (of boiling point 103°-104° C.; $n_D^{20}$: 1.4168) were allowed to run into excess anhydrous hydrofluoric acid (500 ml), at a temperature of about −10° C., in a metallic stirred vessel equipped with a cooler (V2A steel). After completion of the addition, the temperature was allowed to rise to about 15°-18° C. and the reaction was allowed to go to completion at this temperature. When the evolution of hydrogen chloride had ended (after about 4 hours), the mixture was worked up by distillation.

Pivaloyl fluoride is obtained as a liquid of boiling point 67° C. and refractive index $n_D^{20}$: 1.3558; yield, about 80% of theory.

It will be understood that the specification and examples are illustrative but not limitative of the present invention and that other embodiments within the spirit and scope of the invention will suggest themselves to those skilled in the art.

What is claimed is:

1. In a process for the preparation of an acyl cyanide of the formula $$R-CO-CN \qquad (I)$$

wherein

R is an optionally substituted alkyl with 1 to 8 carbon atoms; an optionally substituted cycloalkyl with 3 to 12 carbon atoms; an optionally substituted aryl; an optionally substituted 5- or 6-membered heterocyclic radical which can additionally be fused to a benzine ring, the improvement comprising reacting a carboxylic acid fluoride of the formula $$R-CO-F \qquad (II)$$

in which

R is identified as above, with an alkali metal cyanide, in the absence of a heavy metal salts catalyst or a phase transfer catalyst, at a temperature of from 20° to 150° C.

2. Process as claimed in claim 1 in which the reaction is carried out in the presence of a diluent selected from the group consisting of acetonitule, toluene, xylene, methylene chloride, chlorobenzene, benzonitrile.

3. Process as claimed in claim 1 in which the reaction is carried out without a diluent at a temperature between 60° and 120° C.

4. Process as claimed in claim 1 wherein 0.7 to 1.4 moles of alkali metal cyanide are employed per mole of the carboxylic acid fluoride of formula (II).

5. Process as claimed in claim 1 wherein 1 to 1.25 moles of alkali metal cyanide are employed per mole of the carboxylic acid fluoride of formula (II).

6. Process as claimed in claim 1 wherein R is alkyl of from 4 to 6 carbon atoms.

7. Process as claimed in claim 1 wherein R is substituted alkyl with from 4 to 6 carbon atoms wherein the substituents are at least one of alkoxy with from 1 to 4 carbon atoms; carbaloxy with from 1 to 4 carbon atoms in the alkoxy group; nitro; nitrile and halogen.

8. Process as claimed in claim 1 wherein R is cycloalkyl with from 3 to 6 carbon atoms in the ring system.

9. Process as claimed in claim 1 wherein R is substituted cycloalkyl wherein the substituents are at least one of alkyl, alkoxy or carbalkoxy, each with up to 4 carbon atoms; nitro, nitrile and halogen.

10. Process as claimed in claim 1 wherein R is phenyl or naphthyl.

11. Process as claimed in claim 1 wherein R is substituted phenyl or naphthyl, wherein the substituents are at least one of alkyl, alkoxy, haloalkyl, haloalkoxy or carbalkoxy, each with up to 4 carbon atoms, nitro and halogen.

12. Process as claimed in claim 1 wherein R is a substituted 5- or 6-membered heterocyclic radical containing 1 to 3 hetero atoms in the ring and optionally fused to a benzene ring.

13. Process as claimed in claim 1 wherein R is a substituted 5- or 6-membered heterocyclic radical wherein the substituents are at least one of alkyl, alkoxy or carbalkoxy, each with up to 4 carbon atoms, nitro, nitrile and halogen.

14. Process as claimed in claim 1 wherein

R is an alkyl radical with 4 to 6 carbon atoms, optionally substituted by alkoxy with 1 to 4 carbon atoms, carbalkoxy with 1 to 4 carbon atoms in the alkoxy group, nitro, nitrile and halogen; a cycloalkyl radical with 3 to 6 carbon atoms in the ring system, which is optionally substituted by alkyl, alkoxy, or carbalkoxy, each with up to 4 carbon atoms, nitro, nitrile and halogen; a phenyl or naphthyl radical, which is optionally substituted by alkyl, alkoxy, haloalkyl, haloalkoxy or carbalkoxy, each with up to 4 carbon atoms, nitro and halogen; a substituted 5- or 6-membered heterocylcic radical containing 1 to 3 hetero atoms in the ring and optionally further fused to a benzene ring, and optionally substituted by alkyl, alkoxy or carbalkoxy, each with up to 4 carbon atoms, nitro, nitrile and halogen.

15. Process as claimed in claim 1 wherein the carboxylic acid fluoride is pivaloyl fluoride.

16. Process as claimed in claim 1 wherein the carboxylic acid fluoride is benzoyl fluoride.

17. Process as claimed in claim 1 wherein the carboxylic acid fluoride is 3-trifluoromethyl-benzoyl fluoride.

18. Process as claimed in claim 1 wherein sodium cyanide is used as the alkali metal cyanide.

19. Process as claimed in claim 3 wherein said temperature is between 80° and 100° C.

* * * * *